United States Patent [19]

Johnston et al.

[11] Patent Number: 4,709,698
[45] Date of Patent: Dec. 1, 1987

[54] HEATABLE DILATION CATHETER

[75] Inventors: James H. Johnston, Jackson, Miss.; George D. Hermann, Palo Alto; Tanya A. Atagi, Menlo Park, both of Calif.

[73] Assignee: Thomas J. Fogarty, Palo Alto, Calif.

[21] Appl. No.: 863,089

[22] Filed: May 14, 1986

[51] Int. Cl.⁴ ............................................. A61B 17/36
[52] U.S. Cl. .................. 128/303.12; 128/402; 604/114
[58] Field of Search ... 128/4, 6, 303.1, 303.11–303.13, 128/325, 399–402, 774, 203.27, 204.17, 341–344, 348.1, 200.26; 604/20, 96–103, 113, 114

[56] References Cited

U.S. PATENT DOCUMENTS

| | | | |
|---|---|---|---|
| 659,409 | 10/1900 | Mosher | 128/303.11 |
| 729,171 | 5/1903 | Herrgott | 128/399 |
| 932,775 | 8/1909 | Gaston | 128/303.11 |
| 1,885,106 | 11/1932 | Briggs | 128/303.12 |
| 2,043,083 | 6/1936 | Wappler | 128/303.11 |
| 2,056,678 | 10/1936 | Kolling | 128/303.12 |
| 2,078,686 | 4/1937 | Rowe | 128/303.12 |
| 2,774,445 | 1/1957 | Hart | 128/303.12 |
| 4,038,519 | 7/1977 | Foucras | 604/114 |
| 4,227,535 | 10/1980 | Connor | 128/303.12 |
| 4,315,512 | 2/1982 | Fogarty | 604/97 |

Primary Examiner—Kyle L. Howell
Assistant Examiner—Max F. Hindenburg
Attorney, Agent, or Firm—Limbach, Limbach & Sutton

[57] ABSTRACT

A heatable dilation catheter includes an elongated flexible catheter which has an inflatable balloon attached to its distal end. The balloon has a heating element attached to it. A lumen provides a passageway which allows fluid to be introduced to inflate the balloon so that the heating element is in close proximity to tissue to be treated. The heating element is activated for an appropriate period of time to heat the tissue.

18 Claims, 13 Drawing Figures

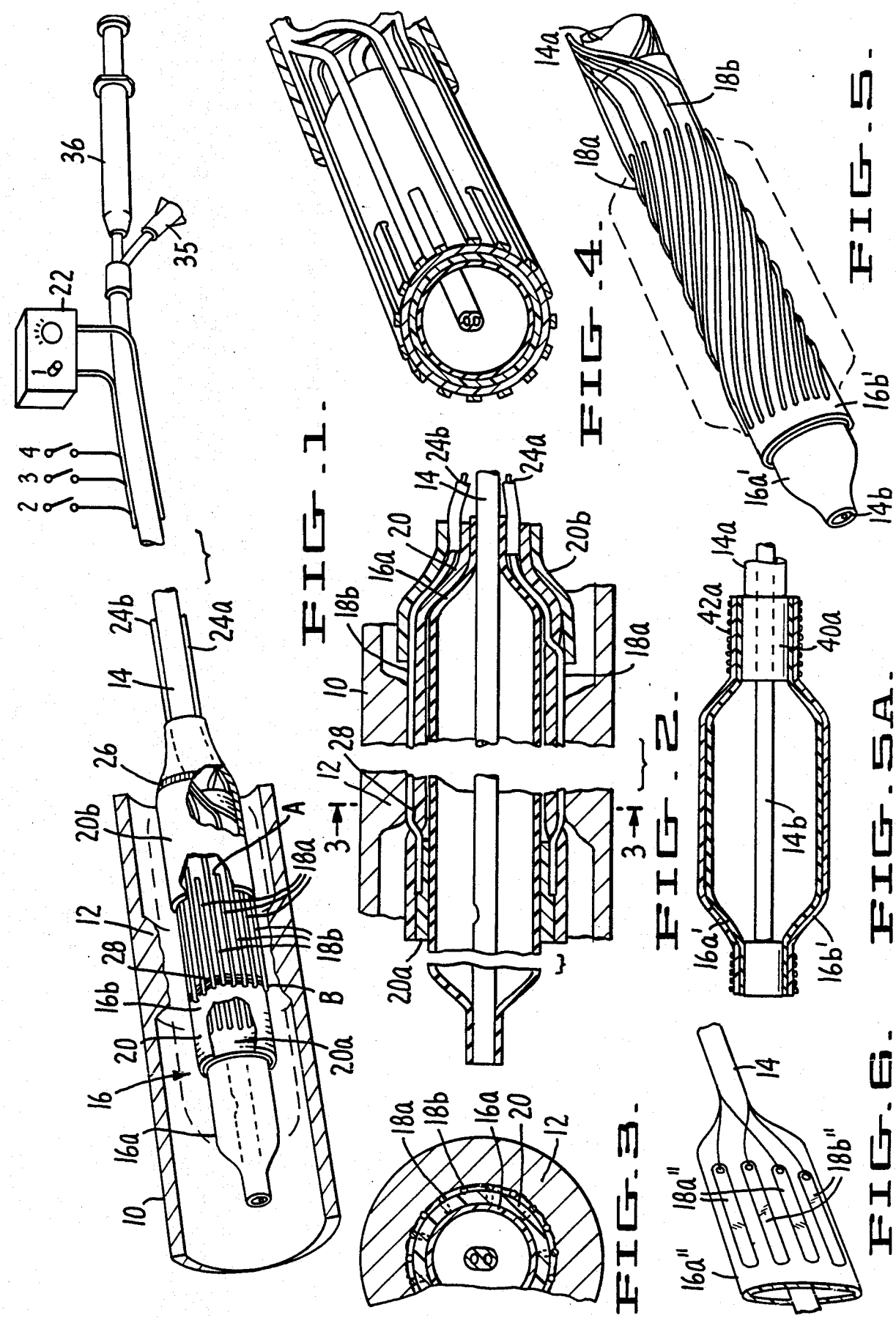

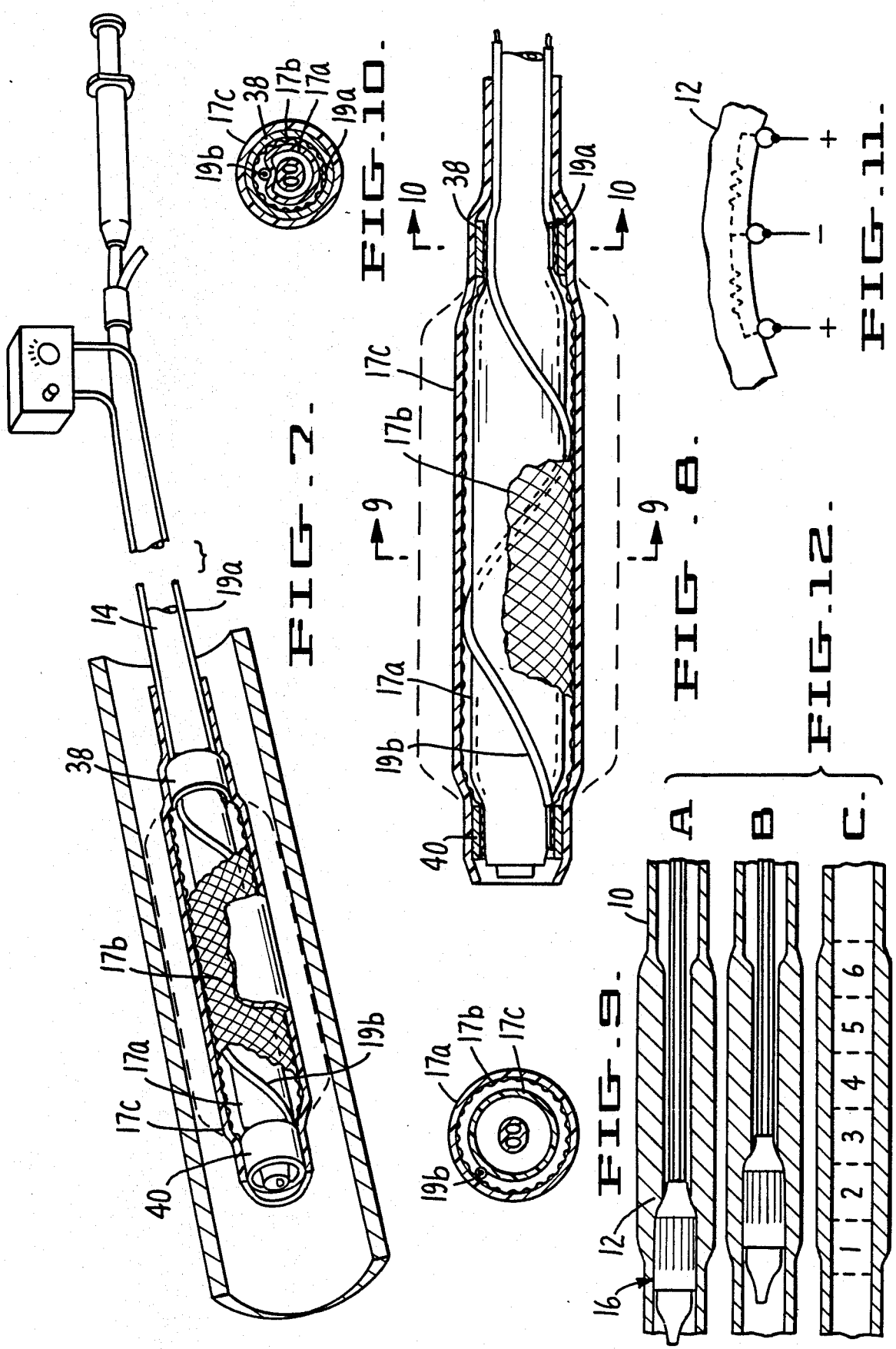

HEATABLE DILATION CATHETER

BACKGROUND OF THE INVENTION

The present invention relates to a method and apparatus for use in dilating and heating tissue, such as in the management of malignant obstructions in a vessel. The invention is particularly concerned with a method and apparatus wherein dilation is achieved through means of a heatable balloon catheter.

Tissue that has been subjected to heat during dilation is more likely to retain its newly dilated configuration than if heat had not been used. Application of heat to tissue gives it a hardened, leathery consistency, probably resulting from denaturization and collagen contraction. These processes occur at moderately elevated temperatures (under 100 degrees C.).

At present, dilation is commonly performed with a set of taper-tipped rigid dilators or, in some cases, with conventional balloon dilation catheters. Neither method incorporates heat. Redilations are common and are often administered frequently (e.g., for esophageal carcinoma). A device that incorporates heat during dilation could significantly reduce the frequency of dilations.

SUMMARY OF THE INVENTION

The present invention provides a heatable balloon catheter which can simultaneously dilate and heat tissue. Use of this apparatus results in a permanency of treatment not achievable by prior art treatment techniques.

The catheter of the present invention includes an elongated flexible lumen which has an inflatable balloon structure attached to its distal end. The balloon structure has an elastomeric heater attached to it. The lumen defines a passageway whereby fluid is introduced into the balloon structure to inflate it to dilate the tissue to be treated and to bring the elastomeric heater into contact with the tissue.

To treat tissue using the catheter of the present invention, the elastomeric heatable balloon structure is positioned in proximity to the tissue to be dilated. The balloon structure is then inflated to both dilate the tissue and to bring the heater into contact with the tissue. Current is applied to the heater for an appropriate time interval. The balloon structure is then deflated and the catheter is removed.

BRIEF DESCRIPTION OF THE DRAWINGS

FIG. 1 is a perspective view illustrating a vessel in the process of being treated by a first preferred embodiment of the invention, with portions broken away and shown in section;

FIG. 2 is an elevational cross-sectional view illustrating the balloon of the first embodiment as the balloon would appear when it is inflated within the vessel;

FIG. 3 is an end cross-sectional view illustrating the heating electrodes of the catheter of the first embodiment in contact with the tissue to be treated when the balloon is inflated;

FIG. 4 is a perspective view illustrating the heating electrodes of the first embodiment;

FIG. 5 is a perspective view illustrating a second embodiment of the invention with solid lines showing helically mounted heating electrodes and dashed lines showing the outline the heating electrodes would take when the balloon is inflated;

FIG. 5A is a schematic elevational cross-sectional view illustrating the second embodiment shown in FIG. 5.

FIG. 6 is a perspective view illustrating a third embodiment of the invention wherein the electrodes comprise conductive paint;

FIG. 7 is a perspective view illustrating a fourth embodiment of the invention, wherein the heater is a conductive braided material, with the balloon structure shown in its collapsed state and with portions broken away and shown in section;

FIG. 8 is an elevational cross-section view illustrating the fourth embodiment with the balloon structure in its collapsed state;

FIG. 9 is a cross-section view illustrating the fourth embodiment taken along line 9—9 in FIG. 8;

FIG. 10 is a cross-section view of the fourth embodiment taken along line 10—10 in FIG. 8;

FIG. 11 is a schematic drawing illustrating the use of tissue as a conductive element for a bipolar heater in accordance with the present invention; and FIGS. 12A–12C are a series of schematic drawings illustrating a method of sequential treatment of tissue in accordance with the present invention.

DESCRIPTION OF THE FIRST EMBODIMENT

FIG. 1 illustrates a vessel 10 and tissue 12 which requires dilation. For example, the vessel 10 may be the gastrointestinal tract which contains a malignant growth. This is the type of malignancy with which the inventive apparatus and method is expected to find primary application. It should be understood, however, that the invention is applicable in treating other types of malignancies, or occluded vessels generally, or wherever dilation of tissue is desired.

The principal elements of the first preferred embodiment shown in FIG. 1 include: a flexible lumen 14; a balloon structure 16, comprising an inflatable balloon 16a and a detachable elastomeric heater 16b, which is attached near the distal end of the lumen 14; and a current generator 22 connected to the heater 16b to provide current thereto.

The lumen 14 is formed of an inert polymer material such as polyethelene and defines a passageway whereby fluid may be introduced into the balloon structure 16 to inflate it.

In the preferred embodiment, the balloon 16a is a length of inert, nonelastomeric polyethelene tubing the ends of which are thermally bonded to the lumen 14.

As shown in FIG. 1, the detachable heater 16b comprises a tube 20 of highly elastic material, such as 0.185"×0.237" medical grade silicone tubing. A first set of spaced-apart electrodes 18a of a first polarity (either positive or negative) extends into the interior of the tube 20 to a point along its length, designated "A" in FIG. 1, at which the electrodes 18a pass upwardly through the wall of the tube 20 and are mounted circumferentially in spaced-apart relationship on the outer surface of the tube 20. A second set of electrodes 18b, of a polarity opposite to that of the first set of electrodes 18a, extends circumferentially along the outer surface of the tube 20 in the spaces between the first set of electrodes 18a. The electrodes 18a are spaced apart from electrodes 18b. Both sets of electrodes 18a and 18b extend along the outer surface of the tube 20 to a point, designated point "B" in FIG. 1, at which they pass downwardly through the wall of the tube 20 and extend for a short distance along its inner wall, as best shown in FIG. 2.

A bushing 20a of elastic tubing, preferably of the same material as that of tube 20, is mounted within the distal end of tube 20 to cover the ends of electrodes 18a and 18b. The interior end of the bushing 20a is aligned with the point (Point B) at which the electrodes 18a and 18b extend downwardly through the tube 20.

A radiopaque marker 28 is formed around the circumference of the bushing 20a at its interior end. The marker is formed by masking all but a short length of the bushing 20a and painting the unmasked portion with curable silicone which contains a radioplaque filler material such as barium sulfate. The radiopaque marker 28 can be used to identify the distal end of the heater electrodes 18a and 18b, as described below.

A protective sheath 20b of elastic tubing, again preferably of the same material as that of tube 20, is mounted over the proximal end of the tube 20 and extends along the length of tube 20 over the point (point A) at which the first set of electrodes 18a passes upwardly through the wall of tube 20. A colored latex marker 26 is formed around the circumference of the sheath 20b near its proximal end. The marker 26 is used for gross positioning of the electrodes 18a and 18b as described below.

Thus, a hollow, detachable bipolar elastomeric heating element 16b is formed which may be slipped over the inflatable balloon 16a for treatment of tissue and then may be removed as desired. Since the heating element 16b is comprised of highly elastic material, it may be detachably mounted on conventional balloon catheters of various sizes to achieve dilation of a desired diameter. Alternatively, it can be permanently mounted on a balloon catheter of a selected size. In the illustrated embodiment, the balloon structure 16, comprising balloon 16a and heating element 16b, has a collapsed diameter of about 8 mm and a maximum inflated diameter of about 16 mm.

The electrodes 18a and 18b are tinned copper wire filaments of about 5-11 mil diameter, with 10 mil diameter being preferred. (It should be understood, however, that the electrodes 18a and 18b can be any conductive material.) The electrodes 18a and 18b are adhered to the tube 20 using curable silicone, such as RTV 3140. The circumferential spacing of the electrodes around the tube 20 is as close as possible without touching in the collapsed state of tube 20 and, preferably, less than 0.125" in the inflated state of tube 20.

As shown in FIG. 1, the electrodes 18a and 18b are connected to lead wires 24a and 24b which are enclosed in silicone tubing and extend from the proximal end of balloon structure 16 to the current generator 22. The silicone tubing is 0.025"×0.047" tubing (0.030"×0.065" or smaller is acceptable.)

In the preferred embodiment, the current generator 22 is a standard high frequency current generator, such as the BICAP from ACMI.

FIG. 1 shows a standard syringe 36 which introduces fluid, such as water or saline, to the balloon 16 through lumen 14.

In the illustrated embodiment, lumen 14 is a dual chamber lumen wherein one chamber serves as the passageway for fluid to be introduced into the balloon structure 16. The fluid passageway has a hole formed in it within the balloon structure 16 for introducing fluid thereto. The second chamber of lumen 14 serves as the tube for a guidewire used in positioning the balloon heating element within a vessel, as will be explained below.

In this first embodiment, as described above, the alternating electrodes 18a and 18b are of opposite polarity and, thus, comprise a bipolar heater. In the illustrated bipolar method of heating, voltage is applied via electrodes 18a and 18b that are exposed directly to the tissue to be treated. As shown in FIG. 11, the tissue acts as a resistive element between adjacent electrodes 18a and 18b. As current conducts through the tissue between the electrodes, the tissue heats up because of its inherent electrical resistance.

This bipolar method of heating the tissue has several significant advantages over other heating methods. First, there is a limited maximum temperature. It is believed that this limit is approximately 100 degrees C., because at this temperature, as the liquid constituents of the tissue begin to boil, they lose their conductivity and, hence, their ability to heat. This inherent temperature limitation greatly reduces the potential for burning or tissue erosion. Second, this method of bipolar heating provides rapid temperature response. Since the heat is generated from within the tissue, there are no intermediate elements to heat up or cool down. This enables the operator to abruptly commence and terminate the period of heating.

To treat tissue, the balloon structure 16 is passed through the vessel 10 over a pre-placed guidewire (which passes through the second chamber of lumen 14 and exits from fitting 35) until the collapsed balloon structure 16 is positioned in proximity to the tissue 12 to be treated, as determined by visual observation of the latex marker 26. The balloon structure 16 is then precisely positioned utilizing X-ray techniques to observe the location of the radiopaque marker 28. The balloon structure 16 is then inflated to dilate the tissue to a desired diameter and to ensure adequate contact between the heating electrodes 18a and 18b and the tissue 12 to be treated. Current is then applied to the heating element 16b for an appropriate time interval. The balloon structure 16 is then deflated and removed from the vessel.

According to a preferred treatment method, illustrated in FIGS. 12A-12C, the bipolar heater 16b is positioned at a first station at the distal end of the tissue 12 to be treated. After treatment at the first station, the heater is withdrawn to a second overlapping station. This procedure is repeated until treatment has been completed at sequential overlapping stations, six in the illustrated case, to provide full coverage of the tissue to be treated.

In a modification of this first preferred embodiment structure, the bipolar heater 16b can be segmented, either circumferentially or longitudinally, to provide selective tissue treatment. For example, the electrodes 18a of a first polarity can be mounted around the circumference of the tube 20 as shown in FIG. 1. However, rather than all of the electrodes 18b of opposite polarity being connected to the same lead wire, the electrodes 18b can be connected to a number of lead wires in electrically parallel groups as shown by the dashed lines and switches 2-4 in FIG. 1. Each group may be selectively turned "on" or "off" to provide heating in specific regions of the heater, e.g., thirds or fourths. This regional heating capability would be particularly useful in cases where the tissue to be treated does not cover the entire inner circumference of the occluded vessel.

DESCRIPTION OF THE SECOND EMBODIMENT

The embodiment of the invention shown in FIG. 5 corresponds to that of the first embodiment shown in FIGS. 1-4 with the exception that the nonelastomeric balloon 16a is replaced by an elastic silicone balloon 16a' and the heating element 16b is replaced by a permanently mounted length of fabric woven material 16b' such as Kevlar. The electrodes 18a and 18b are hand-woven into the fabric in a spiral configuration. The outer surface of the material 16b' may be coated with silicone.

To compensate for axial shrinkage of the fabric material 16b' when the balloon structure is inflated, a sliding lumen arrangement is provided as shown in FIG. 5A. According to this arrangement, the distal end of the balloon 16a'/fabric 16 b' combination is attached to the end of a catheter body 14a. An aluminum bushing 40a is positioned between the inner wall of the balloon 16a' and the catheter body 14a to prevent collapse of the catheter body 14a. The balloon structure is attached with Dacron thread 42a. The other end of the balloon structure is similarly attached to an inner lumen 14b, of the type described above, which is slidable with respect to the catheter body 14a. Thus, the lumen 14a slides when the balloon structure is expanded to allow for axial shrinkage of the fabric material 16b.

DESCRIPTION OF THE THIRD EMBODIMENT

The embodiment of the invention shown in FIG. 6 corresponds to that of the first embodiment with the exception that the entire balloon structure 16 is replaced by a non-elastomeric, polyester balloon 16a" and the electrodes 18a" and 18b" are formed of conductive paint, such as silver-filled acrylic, which is painted on the outer surface of the balloon 16a'.

DESCRIPTION OF THE FOURTH EMBODIMENT

The embodiment of the invention shown in FIGS. 7-10 corresponds structurally to that of the first embodiment with the exception that the balloon 16a is replaced by an elastic polyethelene balloon 17a and the heating element 16b is replaced by a braided stainless steel tube 17b. The tube is coated with an outer layer of silicone 17a.

A lead wire 19a of a first polarity is connected to a first contact sleeve 38. A second lead wire of opposite polarity to that of lead wire 19a is connected to a second contact sleeve 40. The contact sleeves 38 and 40 are mounted in electrical contact with opposite ends of the stainless steel braid heating element 18a to secure the heating element to the lumen 14.

The diameter of the outer balloon collapsed is about 0.220". The diameter of outer balloon inflated is about 0.435".

Thus, this fourth embodiment relies on conventional resistive heating as compared to the bipolar heating techniques described in conjunction with the first three embodiments.

CONCLUSION

Although preferred embodiments of the invention have been illustrated and described, it should be understood that the invention is not limited to the specifics of these embodiments, but rather is defined by the accompanying claims.

What is claimed is:

1. A heatable dilation catheter for simultaneously dilating and heating tissue within a vessel, the catheter comprising:
    an inflatable balloon attached to the distal end of the catheter;
    an elastic heating element mounted on the exterior of the balloon;
    means for introducing fluid into the balloon to inflate the balloon such that the balloon expands to dilate the tissue and to bring the heating element into contact with the tissue; and
    means for activating the elastic heating element to apply heat to the tissue.

2. A heatable dilation catheter as in claim 1, wherein the elastic heating element comprises:
    a tube of elastic material;
    a first set of electrodes of a first polarity mounted circumferentially in spaced-apart relationship on the outer surface of the elastic tube;
    a second set of electrodes of a polarity opposite to that of the first set of electrodes mounted circumferentially on the outer surface of the elastic tube in the spaces between the electrodes of the first set.

3. A heatable dilation catheter as in claim 2 wherein the electrodes of the first set extend along the interior of the tube to a first point at which they pass through the wall of the tube and are mounted circumferentially in spaced-apart relationship on the outer surface of the tube.

4. A heatable dilation catheter as in claim 3 and further including a protective sheath of elastic tubing mounted over the proximal end of the tube and extending along the length of the tube over the first point at which the electrodes of the first set pass upwardly through the wall of the tube.

5. A heatable dilation catheter as in claim 4 and further including a marker formed around the circumference of the protective sheath for use in gross positioning of the heating element within the vessel.

6. A heatable dilation catheter as in claim 2 wherein the electrodes of the first and second sets extend along the outer surface of the tube to a second point at which they pass downwardly through the wall of the tube and extend for a distance along the inner wall of the tube.

7. A heatable dilation catheter as in claim 6 and further including a bushing of elastic tubing mounted within the distal end of the tube to cover the ends of the electrodes of the first and second sets.

8. A heatable dilation catheter as in claim 7 and further including a radiopaque marker formed around the circumference of the bushing for use in precise positioning of the heating element within the vessel.

9. A heatable dilation catheter as in claim 2 wherein the elastic heating element is segmented to provide selective tissue treatment.

10. A heatable dilation catheter as in claim 2 wherein the elastic heating element is detachably mounted.

11. A heatable dilation catheter as in claim 1 wherein the balloon comprises an expandable fabric material having electrodes of opposite polarity woven into the fabric woven material in spaced-apart relationship.

12. A heatable dilation catheter as in claim 11 wherein said electrodes are spirally woven into said fabric woven material.

13. A heatable dilation catheter as in claim 1 wherein the balloon is an elastomeric balloon and the heating element is a conductive tubular material mounted on the outer surface of the elastomeric balloon and comprising braided electrodes of opposite polarity.

14. A heatable dilation catheter as in claim 13 wherein said interwoven braid is stainless steel.

15. A heatable dilation catheter for simultaneously dilating and heating tissue within a vessel, the catheter comprising:
   an inflatable balloon attached to the distal end of the catheter;
   a first set of expandable electrodes of a first polarity mounted circumferentially in spaced-apart relationship on the outer surface of the balloon;
   a second set of expandable electrodes of a polarity opposite to that of the first set of electrodes mounted circumferentially on the outer surface of the balloon in the spaces between the electrodes of the first set;
   means for introducing fluid into the balloon to inflate the balloon such that the balloon expands to dilate the tissue and to expand the electrodes of both the first and second sets into contact with the tissue; and
   means for activating the first and second sets of electrodes such that current conducts through the tissue between electrodes of the first and second sets to heat the tissue.

16. A heatable dilation catheter as in claim 15 wherein the inflatable balloon comprises a non-elastomeric material.

17. A heatable dilation catheter as in claim 16 wherein the non-elastomeric material is polyester.

18. A heatable dilation catheter as in claim 16 wherein both the first and second sets of electrodes comprise conductive paint painted on the outer surface of the non-elastomeric balloon.

* * * * *